US006554852B1

(12) United States Patent
Oberlander

(10) Patent No.: US 6,554,852 B1
(45) Date of Patent: Apr. 29, 2003

(54) MULTI-ANCHOR SUTURE

(76) Inventor: Michael A. Oberlander, 145 Winestone Ct., Alamo, CA (US) 94507

( * ) Notice: Subject to any disclaimer, the term of this patent is extended or adjusted under 35 U.S.C. 154(b) by 251 days.

(21) Appl. No.: 09/645,671

(22) Filed: Aug. 24, 2000

Related U.S. Application Data
(60) Provisional application No. 60/151,423, filed on Aug. 25, 1999.

(51) Int. Cl.$^7$ ............................................. A61B 17/04
(52) U.S. Cl. .......................... 606/232; 606/72; 606/104
(58) Field of Search .................. 606/232, 104, 606/219, 220, 72, 75; 411/457, 921

(56) References Cited

U.S. PATENT DOCUMENTS

| | | | | |
|---|---|---|---|---|
| 3,875,648 A | * | 4/1975 | Bone .......................... | 227/19 |
| 4,635,637 A | * | 1/1987 | Schreiber ..................... | 606/219 |
| 4,696,300 A | * | 9/1987 | Anderson ............... | 273/DIG. 5 |
| 5,224,946 A | * | 7/1993 | Hayhurst et al. ............ | 606/144 |
| 5,324,308 A | * | 6/1994 | Pierce ......................... | 606/232 |
| 5,374,268 A | * | 12/1994 | Sander ........................ | 606/222 |
| 5,522,844 A | * | 6/1996 | Johnson ....................... | 411/447 |
| 5,632,745 A | * | 5/1997 | Schwartz .................... | 606/104 |
| 5,647,874 A | * | 7/1997 | Hayhurst .................... | 606/232 |
| 5,683,401 A | * | 11/1997 | Schmieding et al. ....... | 606/104 |
| 5,690,676 A | * | 11/1997 | DiPoto et al. .............. | 606/232 |
| 5,702,398 A | * | 12/1997 | Tarabishy ................... | 606/104 |
| 5,728,136 A | * | 3/1998 | Thal ........................... | 606/232 |
| 5,810,848 A | * | 9/1998 | Hayhurst .................... | 606/139 |
| 5,827,298 A | * | 10/1998 | Hart et al. .................. | 606/139 |
| 5,997,552 A | * | 12/1999 | Person et al. ............... | 606/139 |
| 6,056,751 A | * | 5/2000 | Fenton, Jr. .................. | 606/151 |
| 6,074,395 A | * | 6/2000 | Trott et al. ................. | 606/104 |
| RE36,974 E | * | 11/2000 | Bonutti ....................... | 606/232 |
| 6,146,387 A | * | 11/2000 | Trott et al. ................. | 606/104 |
| 6,159,235 A | * | 12/2000 | Kim ............................ | 606/232 |
| 6,179,840 B1 | * | 1/2001 | Bowman .................... | 128/899 |
| 6,190,401 B1 | * | 2/2001 | Green et al. ................ | 227/902 |
| 6,334,446 B1 | * | 1/2002 | Beyar ......................... | 128/898 |
| 6,387,113 B1 | * | 5/2002 | Hawkins et al. ......... | 227/180.1 |

FOREIGN PATENT DOCUMENTS

WO    WO 89/01767    *  3/1989

* cited by examiner

Primary Examiner—Rodney M. Lindsey
(74) Attorney, Agent, or Firm—Wallenstein & Wagner, Ltd.

(57) ABSTRACT

A multi-anchor suture is provided which comprises at least two anchors and at least one suture attached to each anchor. The multiple anchors are inserted into a patient's bone and the suture connecting the anchors facilitates reattachment of soft tissue to the bone. Also provided is a method of attaching soft tissue to bone using the inventive multi-anchor suture.

15 Claims, 4 Drawing Sheets

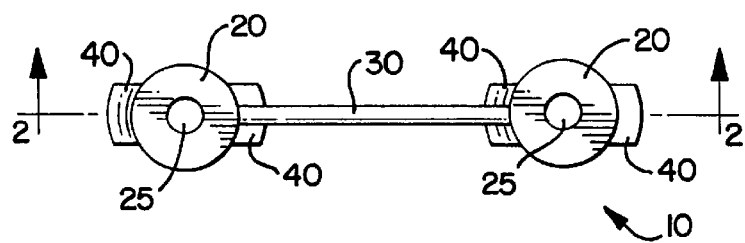
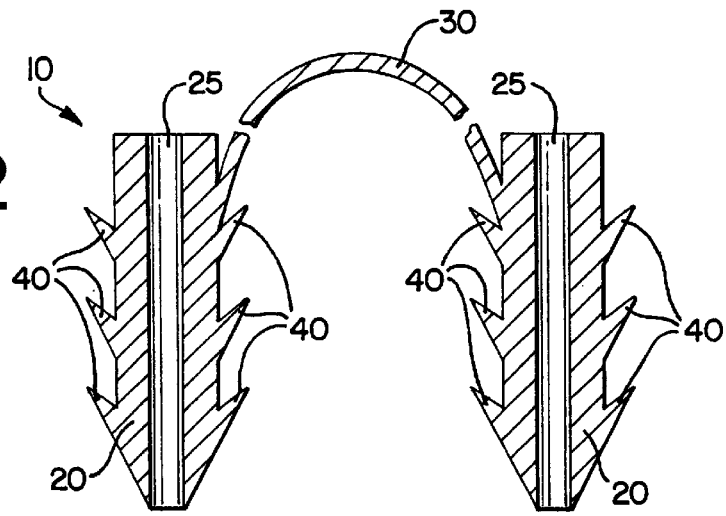
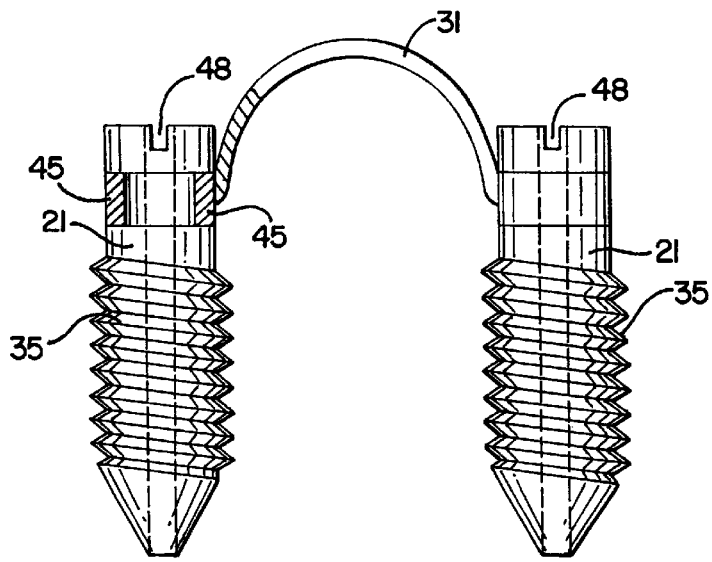
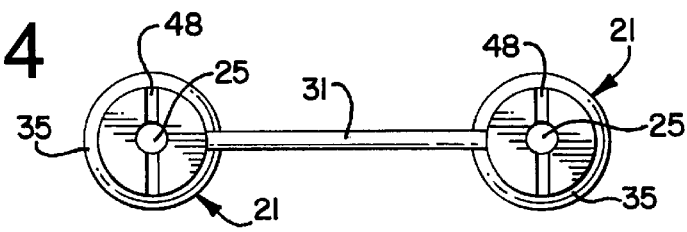

MULTI-ANCHOR SUTURE

CROSS-REFERENCE TO RELATED APPLICATIONS

This application claims the benefit of Provisional application Ser. No. 60/151,423, filed Aug. 25, 1999.

FIELD OF THE INVENTION

The present invention generally relates to the field of medical devices and procedures. More specifically, the invention relates to devices and methods for the re-attachment of soft tissue to bone.

BACKGROUND OF THE INVENTION

Re-attachment of soft tissue to bone is often required in surgery. During athletic endeavors, work, falls, or repetitive use and aging, a ligament or tendon may be pathologically avulsed or torn from its normal insertion site. Soft tissue to bone re-attachment is then needed to return normal or near normal function to the limb or joint. Such re-attachment may be necessary anywhere within the body, including, by way of example but not by way of limitation, in the wrist, ankle, knee, or shoulder. Re-attachment is considered important for several reasons. First, it helps ensure proper healing. When a ligament has been torn away from its normal position of attachment to bone it may become bathed in synovial fluid, which is a poor healing environment. Second, even if the ligament does heal, it may heal in a stretched out or elongated position, possibly leading to residual joint laxity or dysfunction. Surgical repair may thereby become necessary to return proper structure and function to the joint. The present invention relates to the fixation of soft tissue to bone at its proper location and is suitable for use in many common surgical procedures including, by way of example but not limitation, rotator cuff repair, bankart repair, ligament avulsions from bone (knee, ankle, shoulder, wrist) and many others known to those of skill in the art. While the invention is suitable for use in open surgery, it is particularly useful for arthroscopic surgery.

The present invention is more fully described below. Many publications are cited herein and the entire disclosure of each such cited reference is hereby incorporated by reference in its entirety, and should be considered a part of this disclosure as if set forth in its entirety at the point of reference.

Several approaches for attaching soft tissue to bone exist in the art. Each suffers disadvantages.

One approach requires transosossous suture tunnels. The use of such tunnels is described more fully in *Shoulder Reconstruction* by Charles S. Neer II (W. B. Saunders Co. 1990). Although appropriate for some cases, the use of bone tunnels can be difficult and generally requires large open incisions.

Another approach, which is especially useful in closed, arthroscopic or endoscopic settings, involves the use of suture anchors that allow quick fixation without the need for extensive exposure. A common problem among many such anchor systems is that they require knot tying of the attached sutures after the suture anchors are inserted into the bone and the sutures placed through the soft tissue.

One example of a suture anchor assembly is set forth in U.S. Pat. No. 5,441,502, which describes an anchor assembly having a pre-threaded suture positioned at the posterior of the anchor. After the suture anchor is properly deployed in the bone, the associated suture extends upwardly through the soft tissue. The free ends of the sutures are then tied to secure the soft tissue to the bone.

An important limitation of this prior art is the requirement for knot tying. Knot tying itself is time consuming and technically demanding, especially in an arthroscopic environment, where surgery is done in small spaces through small incisions. In addition, knot slippage or suture breakage during knot tying could lead to unsecured attachment of the soft tissue to bone, potentially adversely affecting the healing process.

Some non-suture anchor systems have been described, such as in U.S. Pat. Nos. 5,840,078, 5,013,316, and 4,532,926. However, fixation with these devices may not be as secure as that achieved with sutures. In addition, non-suture anchors offer fewer points of fixation, typically providing only one point of soft tissue to device fixation per device, and one point of device to bone fixation per device.

Staple-like devices have been used surgically to eliminate the need for suturing outside of the soft-tissue to bone context. U.S. Pat. Nos. 4,994,073 and 5,089,009 describe surgical skin fasteners that eliminate the need for suturing when joining adjacent portions of soft tissue. The fastener comprises a backspan and two prongs depending therefrom. The skin fasteners are mostly useful for joining two edges of body tissue together or for joining layers of tissue both laterally or laminarly as required in skin grafting. Other surgical tacks made of bioabsorbable material such as the bankart tack (Bionix) and the Suretek (Acufex) leave hard polylactic or polyglycolic acid portions of the tack exposed. These exposed hard polymers pose potential injury to the articular cartilage or if broken off, may result in loose bodies, which may cause further joint deterioration or mechanical symptoms.

Staple-like devices have also been used for attaching bone to bone. U.S. Pat. No. 4,994,063 describes a bone staple with two feet and a central web portion made of rigid material. Portions of bone on opposite sides of a fracture are compressed toward each other by inserting the two feet of the staple into each bone portion and crimping the central web portion of the staple.

Staple-like devices having large rigid bodies have also been used to attach artificial soft tissue to bone. U.S. Pat. No. 4,793,335 describes a bone implant composed of a deformable metal plate and a pair of anchor pins attached to and extending from the metal plate. The staple described therein is used to hold a tendon or ligament over a relatively large area. These staples are not suitable for intra-articular usage because they tend to loosen in time with cyclical loading of the tissues and may become a loose object within the joint, causing further injury.

SUMMARY OF THE INVENTION

The invention relates to devices and methods for re-attaching soft tissue to bone. The invention is based in part on the discovery of an assembly comprising at least one suture joining multiple cannulated or non-cannulated anchors. This invention also relates to cannulated instruments to apply the suture-anchor assembly. Although the invention includes within its scope assemblies comprising multiple sutures or multiple anchors, in one embodiment a single suture is joined by two cannulated anchors. In this embodiment, the two cannulated anchors joined by suture can be easily and precisely inserted over guide wires at an optimal point of fixation through one larger arthroscopic cannula, thereby providing a knotless mechanism for attachment of soft tissue to bone having two points of fixation for a single suture. The invention thereby avoids the problems of the prior art associated with knot tying while at the same time providing improved structural and performance characteristics such as increased number of points of fixation per suture and facilitated arthroscopic insertion and placement. The invention also minimizes the risk of a portion of the device breaking off and becoming loose within the joint.

As used herein, the word "re-attach," and all forms thereof such as "re-attached," "re-attachment," and "re-attaching," is intended to include not only its ordinary meaning but also the concept of "attach." Therefore, the term will be understood to properly describe any situation in which components are being attached, regardless of whether they had been attached previously.

In accordance with one aspect of the present invention, a system for attaching soft tissue to bone is provided. The system is composed of one integrated assembly. The integrated assembly is composed of at least two anchors, each having a region for insertion into the bone and a region for suture connection and at least one knotless suture attached to the suture connection region of each anchor. In one embodiment, at least one or both of the anchors is cannulated.

In accordance with another aspect of the present invention, the assembly includes the suture being attached eccentrically to the insertion region of at least one of the anchors.

In accordance with another aspect of the present invention, the system further includes a gun for firing the assembly.

In accordance with another aspect of the present invention, the system further includes a grasper tool having at least one cannulated barrel.

In accordance with still another aspect of the present invention, the system includes an initial anchor impactor tool and a final impactor tool, each of said tools adapted to apply force to at least one of the anchors for insertion into soft tissue and/or bone.

In accordance with still another aspect of the present invention, the system for attaching soft tissue to bone includes an assembly that is composed of at least two anchors, each having a region for insertion into the bone and a region for suture connection. The region for suture connection on at least one anchor includes a rotatable collar that can rotate relative to that anchor so that the suture is prevented from rotational movement with the anchor as the anchor is rotated, such as during insertion into the bone or other areas.

In accordance with still another aspect of the present invention, a method for attaching soft tissue to bone is provided. The method includes inserting at least two guidewires through the soft tissue and into the bone, inserting at least two anchors along the guidewires with the anchors being connected by a suture and thereafter inserting the anchors into the bone.

In accordance with another aspect of the present invention, a method for attaching soft tissue to bone is provided that comprises providing an assembly for attaching soft tissue to bone wherein the assembly is composed of at least two anchors, each anchor having an insertion region for insertion into the bone and a suture region for suture connection and a suture attached to the suture connection region of each anchor into the bone while the suture is attached to the suture connection region of each anchor.

BRIEF DESCRIPTION OF THE DRAWINGS

FIG. 1 is a top view of the preferred embodiment of a dual-anchor according to the present invention.

FIG. 2 is a side sectional view of the dual-anchor embodiment of FIG. 1 taken along line 2—2 of FIG. 1.

FIG. 3 is a side elevation view, partly in section, of another dual-anchor embodiment in accordance with the present invention.

FIG. 4 is a top view of the dual-anchor embodiment of FIG. 3.

DETAILED DESCRIPTION OF THE INVENTION

Figure 5:
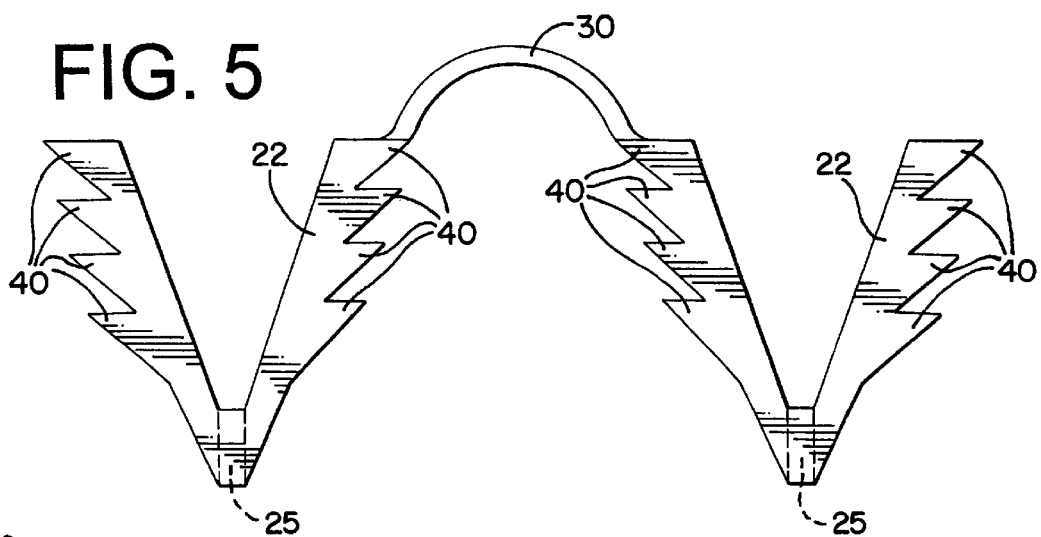
FIG. 5 is a side elevation view of another dual-anchor embodiment according to the invention.

The present invention provides a knotless suture anchor assembly for use in attaching soft tissue to bone having more points of fixation per suture than the prior art. Although useful in an open setting, the assembly of the invention is especially well suited for use in a closed, or arthroscopic or endoscopic setting.

In accordance with the invention, the assembly comprises two or more anchors. The anchors comprise at least two regions: a region for insertion into the bone and a region for suture attachment. The invention encompasses anchors in which the two regions overlap in their entirety, in part, and not at all.

The anchors of the invention may be cannulated or non-cannulated. For ease of positioning and inserting the anchors in the bone, cannulated anchors are preferred. FIGS. 1 and 2 show the sectional and side views of the preferred embodiment of the dual-anchor suture. Dual-anchor suture 10 has two anchors 20. A typical anchor is approximately 1 to 1.5 centimeters in length and 4–5 millimeters in width. Anchor 20 tapers slightly near its bottom end but does not need to form a sharp point. In the preferred embodiment, both anchors 20 are identical but it is understood that they can be of different dimensions or materials. For cannulated anchors, round opening 25 may run through the entire body of anchor 20. These may be of star design to facilitate insertion in an arthroscopic environment.

On each of the anchors 20, there is at least one barb 40 oriented in a way that facilitates the insertion of the anchors into soft tissue and bone but prevents the anchors from pulling out. Barbs 40 are typically 2 millimeters in length. As illustrated, preferably the barbs are situated at a 45–60 degree angle from the anchor body. Although only two rows of three barbs are visible on FIG. 2 on each anchor, additional rows of barbs are usually present. The preferred number of barbs in each row depends on the size of each anchor. Generally, making the barbs thicker or bigger or increasing the number of barbs on an anchor will increase the probability that the anchor will be firmly imbedded in the bone, therefore increasing the pull-out strength, but also increase the size of the hole in the bone.

As it is shown in the drawings of FIGS. 1 and 2, the anchors 20 are bridged with a suture 30. Suture 30 is typically slightly shorter than the length of the anchors, approximately 1 centimeter. The suture can be molded directly into the anchor during manufacture of the same or otherwise fixed to the anchor prior to insertion into a patient's bone. The suture may be fixed to each anchor approximately one-third or one-half of the distance from the top of the anchor.

While the dual-anchor suture described above can be implanted utilizing open surgery procedures, it is within the scope of this invention to adapt the multi-anchor suture for arthroscopic use. Arthroscopic surgery is less invasive and promotes faster healing and recovery for the patient. Multiple anchor systems are cannulated for arthroscopic use.

The anchors of the invention need not have a cannula that extends through the center vertical axis of anchor 20. The anchors of the invention may have a cannula that is off-center. As described in detail below, the cannulation of the anchors permits insertion of an anchor along a guide wire, thereby facilitating proper placement of the anchor and helping to avoid inadvertent dropping of the anchor into the surgical wound area.

The anchors of the invention are able to become well attached to the bone to prevent inadvertent removal. To facilitate or strengthen this attachment, the anchors may be conical in shape. The anchors of the invention may also have other shapes, as shape, alone, is not the only method within the scope of the invention for ensuring proper attachment of the anchor to bone. Anchors having barbs or flanges or threads, and any other protrusion or invaginations are also within the scope of the invention. In addition, anchors having a surface coated with an adhesive material or comprising an adhesive component are also within the scope of the invention. Any anchor having an outside surface having a shape or composition that is adapted to adhere to bone is within the scope of the invention.

FIGS. 3 and 4 illustrate another example of the dual-anchor system. Anchors 21 have regions for connection to suture 31 and regions for tissue insertion. The exterior of anchors 21 have threads 35 for insertion and fixation in the soft tissue and bone mass by screwing anchors 21 into the bone mass and/or soft tissue. As the shape and structure of the anchors of the invention can vary in unlimited ways, different insertion instruments will be adapted to facilitate the insertion of the different variations of the invention into soft tissue and bone.

As is well within the skill in the art to determine, it may also be preferable that an anchor of the invention, especially one having a threaded exterior, also be equipped with a region 48 that is adapted for receiving an applied torsional force. Such a region, or portion thereof, may be so adapted to be slotted like the head of a standard screw, or to be polygonal like an exterior surface of a standard nut, or to have a polygonal or star shaped cavity therein, such as the cavity typically found in the head of a screw that is adapted to receive an Allen wrench, or to have any of the many other similar shapes well known in the fastener art, or any other shape that is adapted to receive an applied torsional force.

Preferably, region 48 is star shaped. During twisting of anchor 21, it is important that suture 30 not wrap around anchor 20 and weaken, break off or lose some of the effective length of the suture. In FIG. 3, collar 45 of left anchor 21 is illustrated in sectional view to show how collar 45 rotates independent of anchor 21. Collar 45 rotates about the anchor so that suture 31 does not wrap around the anchor during insertion and twisting of the anchor into the bone. Preferably, collar 45 is made of the same material as anchor 21. Suture 31 is molded directly into collar 45. Alternatively, instead of collar 45, suture 31 may form a loop around anchor 21 that performs a similar function as collar 45 does.

FIG. 5 illustrates yet another example of the dual-anchor suture 10. Flexible anchors 22 are in an approximate V-shape and collapse upon insertion into the bone. In this embodiment, the suture is fixed to the end of the top barb of each anchor.

The anchors of the invention include anchors made of bioabsorbable materials as well as anchors made of non-bioabsorbable materials. Bioabsorbable materials within the scope of the invention include polyglycolic acid, polylactic acid, and co-polymers of polylactic acid and polyglycolic acid. Other bioabsorbable materials within the scope of the invention are well known in the art and are described more fully in "Orthopedic Applications for PLA-PGA Biodegradable Polymers," *Arthroscopy* Vol. 14: 726–37 (1998), by K A Athanaion, et al. A preferred bioabsorbable resinous material for constructing the anchors of the present invention is disclosed in Kaplan et al., U.S. Pat. No. 4,523,591. Non-bioabsorbable materials within the scope of the invention include stainless steel or titanium. Other non-bioabsorbable materials are also within the scope of the invention. If metallic suture anchors are used, to avoid joint destruction, no metal should protrude from bone or appear in the articular surface of any joint.

The anchors of the invention are connected at their connection regions by one or more sutures. The preferred suture materials are either non-absorbable or absorbable materials having long half life. Appropriate suture materials include absorbable materials such as Vicryl and Panacryl and non-absorbable materials such as Dexon, Ethibond, and Tevdeck. These materials are available from commercial sources such as United States Surgical Corp. of Norwalk, Conn. and Ethicon, a subdivision of Johnson & Johnson of Rutherford, N.J.

The suture can be connected eccentrically to the anchors. The eccentric position of the suture on the anchor will cause at least the insertion region to rotate or turn when tension is applied to the anchors. This rotating motion will lock the anchors into bone, fortifying the affixation of soft tissue to bone.

An important advantage of the present invention is that no knot in the suture is necessary. The need for suture knots is avoided because the sutures of the invention are tethered by more than one anchor. The problems of knot tying and potential knot slippage are thereby avoided. In addition, once inserted inside the exact place, the multi-anchor suture holds the tissue and bone in place and creates multiple points of fixation—for example, anchors vertically holding soft tissue to bone and the connecting suture member forming a horizontal mattress suture. Thus, the invention provides more than one point of suture to device fixation per device and more than one point of device to bone fixation per device.

In accordance with the invention, the assembly may comprise two or more anchors and one or more sutures.

Assemblies having more anchors than sutures are within the scope of the invention, as are assemblies having fewer anchors than sutures, as well as assemblies having the same number of anchors and sutures. Anchors with connection regions having larger geometries may be particularly well suited for use in assemblies having a ratio of sutures to anchors that is greater than otherwise, especially if greater than one.

Although the assembly according to the invention may include more than two anchors and more than one suture, a full understanding of the operation and benefits of the invention may most easily be grasped from a review of an example having only two anchors and one suture. Accordingly, instruments for insertion of anchor assemblies will also be illustrated as those for an assembly having two anchors and one suture. However, the discussion of this exemplary assembly is intended only to provide an illustrative example and is not intended to limit the scope of the claimed invention in any way. Neither are the instruments for anchor insertion limited to those adopted for the exemplary anchor assembly.

For purposes of the discussion of this example, the following background information is useful: a bone surface is prepared for surgery. An area of tendon or ligament avulsion is exposed and prepared for attachment of soft tissue to bone. Preparation of the bone surface creates a bleeding bed to ensure an adequate blood supply and scar tissue formation for proper soft tissue and bone healing.

Arthroscopic insertion of the dual-anchor suture may be performed inside of an arthroscopic cannula. Such arthroscopic cannulae are well known in the art including, for example, in U.S. Pat. No. 5,840,078, which describes a soft tissue positioning instrument. Such cannulae are well known in the art and are readily available from Arthrex of Naples, Fla., Acufex of Smith & Nephew, Inc. of Andover, Mass., and Surgical Dynamics of Norwalk, Conn. The arthroscopic cannula allows insertion of instruments and anchors without the risk of catching or being wrapped up in soft tissue. The cannula also may provide an arthroscopic surgical work area.

A double cannulated tubular guide, grasper, or trochar is then inserted telescopically through the arthroscopic cannula. Appropriate guides are well known in the art and are readily available from Arthrex, Smith & Nephew, Inc., Linvatec Corp. of Largo, Fla., and Bionx Implants Inc. of Blue Bell, Pa. The guide may have spikes at a distal end to hold soft tissue to bone. This ensures adequate soft tissue capture and exact location of the suture anchors.

Figure 6:
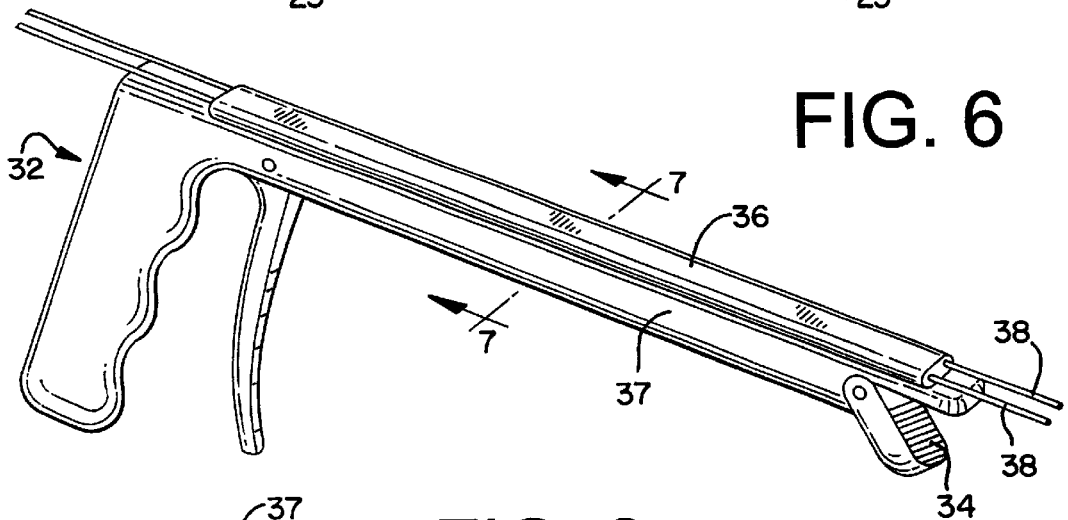
FIG. 6 is a perspective view of the grasper tool according to the present invention.

FIG. 6 shows a perspective view of grasper 32 adapted for a dual-anchor suture of the invention. A pair of cannulated barrels 36 are joined on top of grasper body 37. The barrels 36 can also be fixed below the grasper body 37. Grasper 32 has a jaw 34 at the distal end to grasp soft tissue at a certain location.

Figure 7:
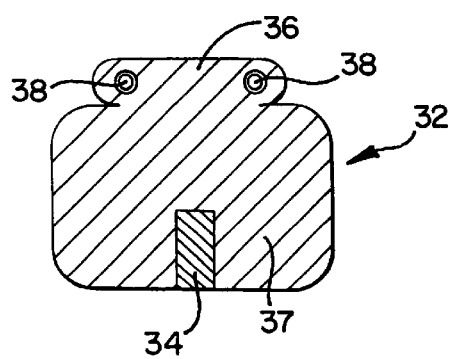
FIG. 7 is a sectional view of the grasper tool of FIG. 6 taken along line 7—7 of FIG. 6.

FIG. 7 is a sectional view of the grasper adapted for the current invention. The pair of barrels 36 are cannulated to allow guide wires 38 to go through. There need be sufficient clearance between barrels 36 and jaw 34 to permit insertion of wires 38. The two barrels 36 are at a small distance apart from each other. This distance can be approximately 6 mm, depending on the diameter of each anchor and the length of the suture. This distance will allow sufficient horizontal bone bridge between two anchors.

Figure 8:
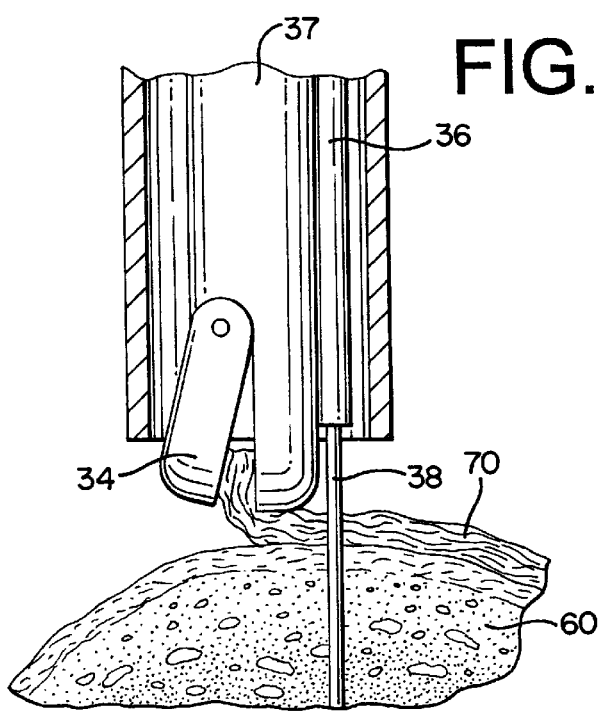
FIG. 8 is a side view, partly in section, showing use of the grasper tool according to the present invention.

Turning now to FIG. 8, grasper 32 is used to control the location of soft tissue 70. A pair of guide wires 38, or K-wires, are then inserted into soft tissue 70 and bone 60 through the tubular guides or the double barrels connected with a grasper. Such guide wires are well known in the art and are readily available from DePuy OrthoTech of Tracy, Calif. The guide wires are drilled into bone to a pre-marked line on the wires, typically about 1.5 to 2.0 centimeters from the end of the, wires (and thus, 1.5 to 2.0 centimeters into the bone). Alternatively, the wires may be attached to the bone by means other than drilling, such as by taping. This preliminarily secures the soft tissue to the bone and will facilitate insertion of the anchors in the bone mass.

Figure 9:
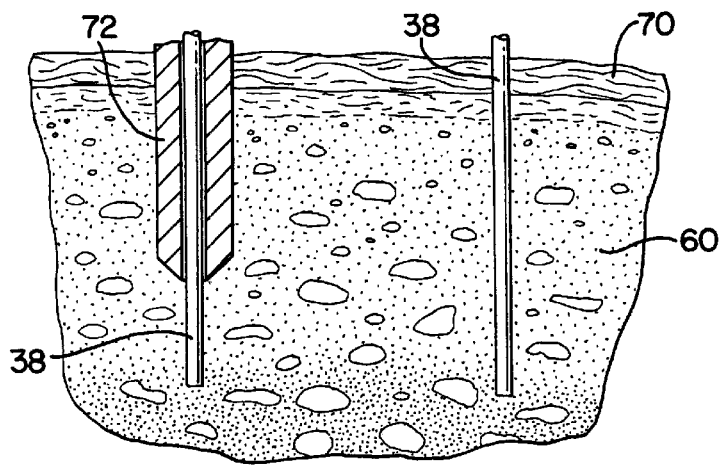
FIG. 9 is a side view, partly in section, showing use of the drill bit according to the present invention.

As illustrated in FIG. 9 cannulated drill 72 bit may then be inserted over guide wires 38 and used to bore into the surface of the bone 60 in the area where the guide wire is inserted thereby forming a bore in the bone that is adapted to receive the anchors. Typically, the bone is bored to a depth of approximately 8 millimeters. A drill bit may be used over each guide wire 38. Appropriate drill bits and drill mechanisms also are well known in the art and are readily available from Arthrex, Bionx Implants, Inc., and Innovasive Devices, Inc. of Marlborough, Mass. Alternatively, no bore may be needed. The drill bit will also have a scribe marking to ensure a sufficient channel for insertion of the anchor.

Figure 10:
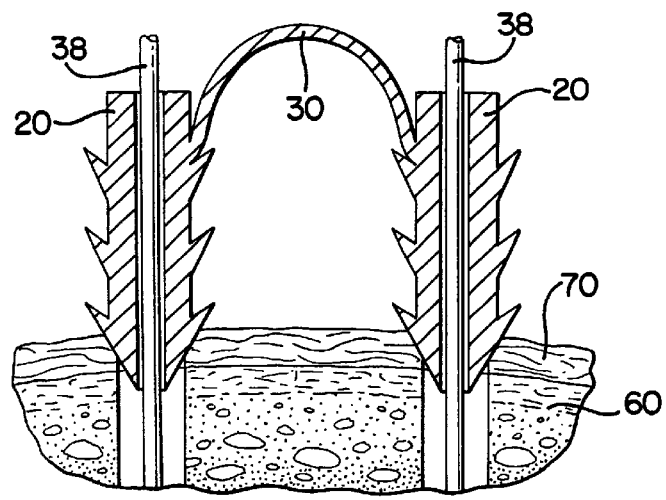
FIG. 10 is a side sectional view showing insertion of the dual-anchor into the bone according to the present invention.

FIG. 10 illustrates the cannulated suture anchors being inserted over the guide wires 38 and into the bores. Opening 25 on each end anchor 20 is slightly larger than the cross section of wires 38. It is understood that although opening 25 and wire 38 preferably have a circular cross section, any cross-sectional shapes will work, including square and elliptical, as long as anchor 20 can fit over wire 38. Anchors 20 slide down wire 38 into position. Barbs 40 may bend slightly during insertion of the anchor into the bone. A pair of cannulated tamps can help seat the dual-anchor suture 10 and counter-sink the anchors. Cannulated tamps are well known in the art and are readily available from Bionx Implants Inc. and Acufex of Smith & Nephew, Inc.

Figure 11:
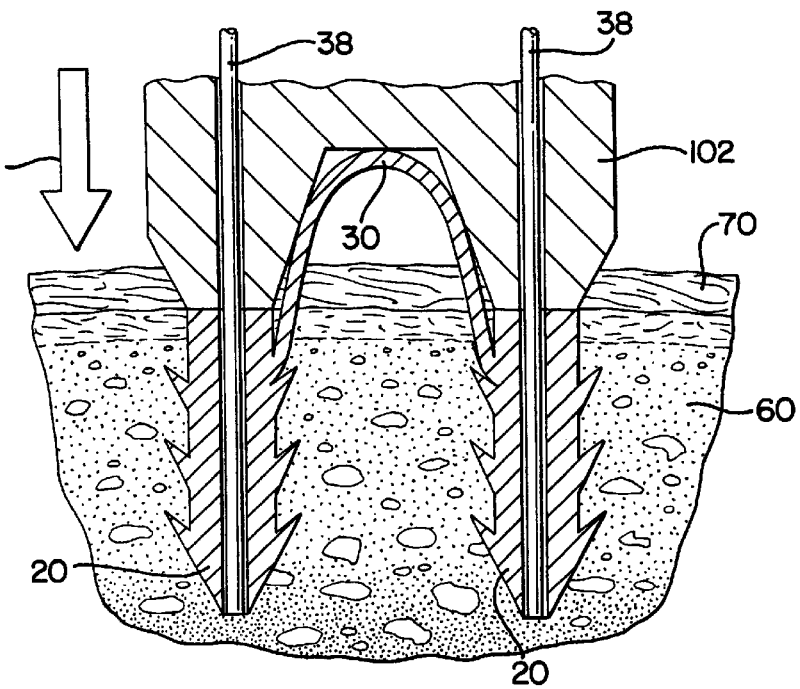
FIG. 11 is a side sectional view showing use of an initial anchor impactor according to the present invention.
Figure 12:
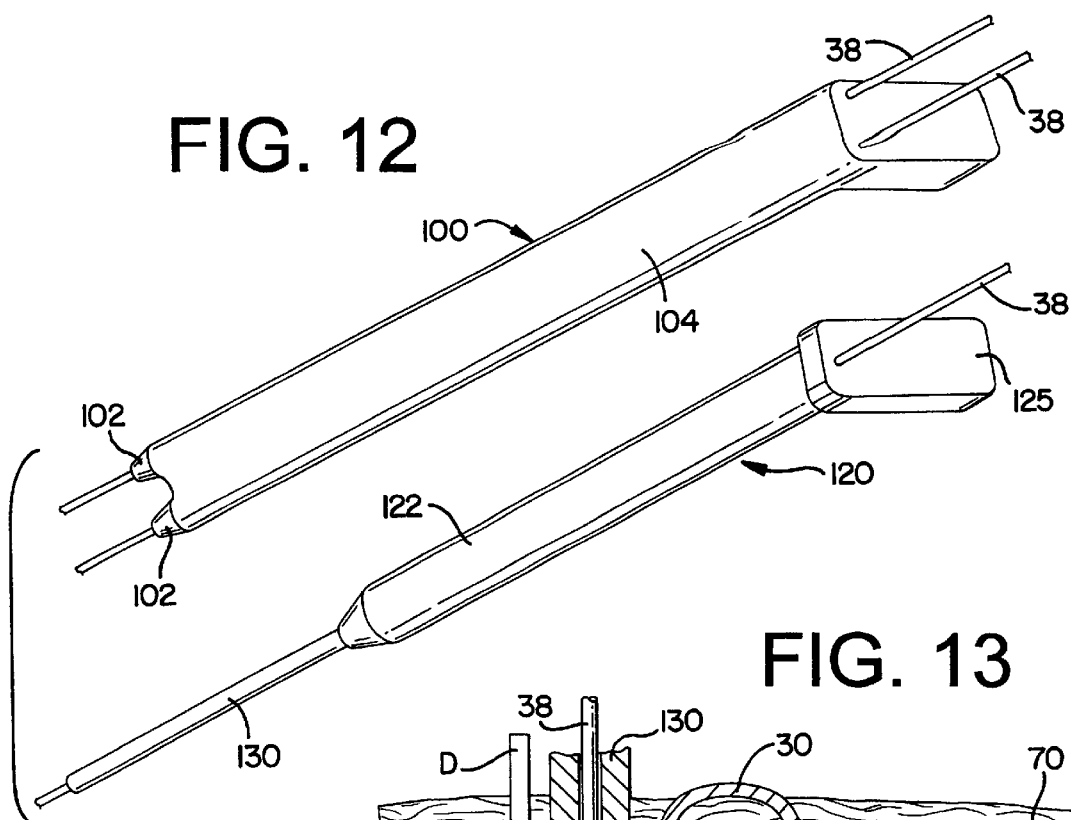
FIG. 12 is a perspective view of the initial anchor impactor and a final impactor in accordance with the present invention.

Alternatively, an initial anchor impactor is adapted for the current invention. FIG. 11 shows use of an initial anchor impactor 100 and FIG. 12 shows a side view of impactor 100. The initial impactor 100 has a tubular body 104 that is double cannulated for passing through a pair of guide wires 38. The initial impactor 100 has an extended protrusion platform 102 at its distal end. Although FIG. 12 shows platform 102 on one side of the tubular body 104, this platform can be on either or both sides of the tubular body 104. In addition, platform 102 can be of any size or shape as long as it allows a mallet to tap the initial impactor 100 down to help insertion of the suture anchors. A region of the initial impactor 100 is shaped to fit the top of the suture anchors, allowing even pressure on the anchors in direction D. Initial impactors are made of strong materials suitable for surgical use such as 316 L stainless steel or other similar metal alloy.

An initial anchor impactor as shown in FIGS. 10 and 11 can push the suture anchors down into soft tissue and bone to the same level. However, insertion using an initial anchor impactor may only put the anchors partially through soft tissue and bone. A final impactor 120 may be needed to complete insertion of the suture anchors and tensioning of the suture material, thus optimizing soft tissue attachment to bone.

Figure 13:
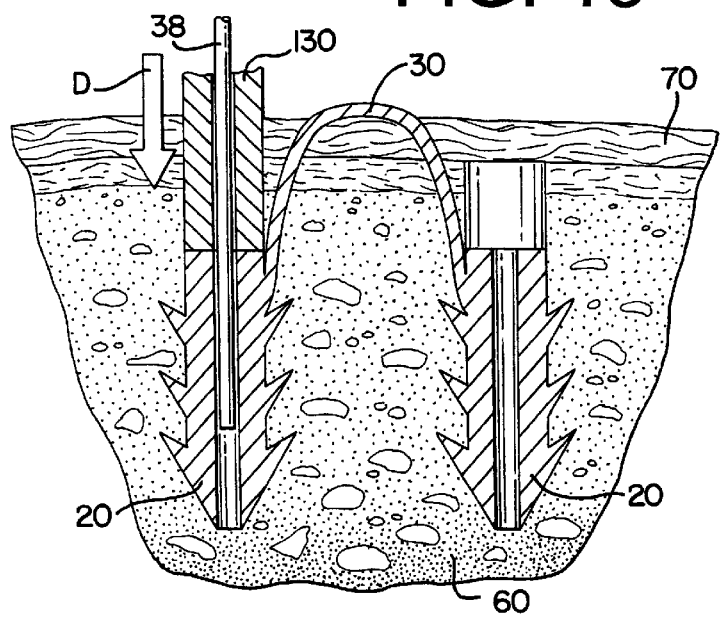
FIG. 13 is a side sectional view showing use of the final impactor in accordance with the present invention.

Referring now to FIGS. 12 and 13, a final impactor or tensioner 120 having a single cannula is used to tension the suture and fully impact each anchor into the bone. The final impactor is cannulated so that it can be inserted along a guide wire to reach the anchors. The final impactor 120 has an elongated tubular body 122. A region of the final impactor has a handle 125 that extends perpendicular to the longitudinal axis of the tubular body 122. The handle 125 can be on any side or both sides of the tubular body 122 and can be of any shape or size as long as force can be applied to the handle to tap down an anchor into bone. The final impactor 120 has a region 130 adapted to operatively engage the top of an anchor so as to permit downward force in direction D to be transmitted to the anchor. Region 130 is approximately the same size as the top of anchor 20. Final impactor 120 is utilized separately on each anchor. It is preferable that anchors 20 are inserted into the bone so that the top of anchor 20 is approximately 5–6 millimeters into the bone. At this point, suture 30 will be taut locking soft tissue 70 adjacent to bone 60. Like an initial anchor impactor, a final impactor can be made of 316 L stainless steel or similar strength alloy.

Complete seating of the anchors in the bone can be done by alternating the single final impactor over each guide wire and slightly tapping each anchor into place. Complete seating of the anchor suture forms vertical anchor fixations as well as a horizontal mattress suture. With the impactor in place, the guide wire can then be removed with pliers or a drill. The same technique can be repeated to remove the rest of guide wires.

Other instruments can also be adapted for use with the multi-anchor suture assembly of the invention. One such alternative is a gun pre-loaded with the anchor suture assemblies. A gun can be used to deliver non-cannulated anchor suture as well as cannulated suture assemblies. Guns for delivery of non-cannulated anchors have been described previously by Surgical Dynamics of Norwalk, Conn.

A gun may also be cannulated to fire cannulated multi-anchor suture assemblies into soft tissue and bone. A gun having cannulated holes can be pre-loaded with cannulated anchor assemblies. The gun can then be fit over guide wires for exact placement of the anchor assemblies. The anchor assemblies can then be fired with sufficient velocity to penetrate soft tissue and bone. Using a gun to deliver a multi-anchor suture may eliminate the need for pre-drilling holes and avoid the use of additional instrumentation. Anchor insertion with guns may be significantly faster where multiple insertions are necessary.

Figure 14:
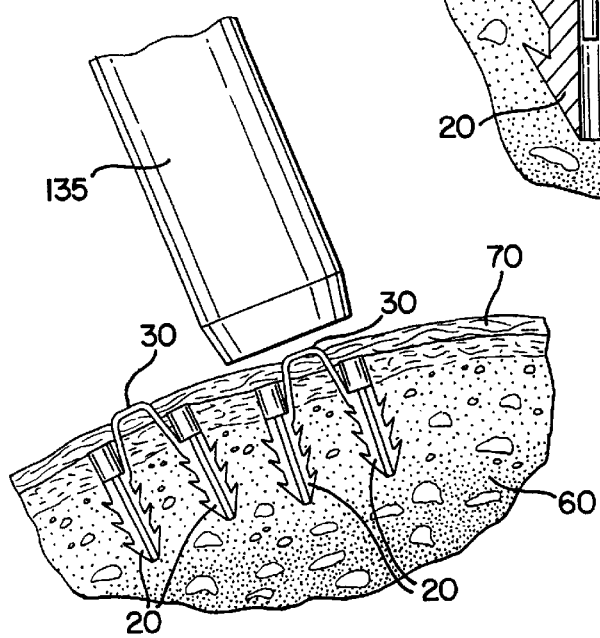
FIG. 14 is a side view, partly in section, of a reattachment of soft tissue to bone utilizing the present invention.

Depending on the surgical situation, a single or multiple anchor suture assemblies may be needed to accomplish proper repairs of soft tissue to bone connection. As is well within the skill in the art to recognize and perform, and depending upon the type and severity of the soft tissue to bone attachment that is required, more than one device of the invention may be used in concert. For example, multiple dual-anchor sutures may be required. FIG. 14 illustrates a cross-sectional view of soft tissue-bone attachment using more than one dual-anchor suture. As one integrated assembly, the suture anchor 10 is inserted through soft tissue and bone. The multiple anchors of one suture assembly provide multiple points of vertical fixation. In addition, the suture assembly provides horizontal tension to strengthen soft tissue to bone attachment. Each anchor may be separated by distances such as at least 5 mm to leave some bony bridge between the anchors. For multiple suture assemblies, the anchors may be staggered from the edge of the tuberosity toward the joint by distances including 5 mm. Multiple insertions of the anchor suture assemblies expand the area for soft tissue to bone repair.

It would be within the skill in the art based upon this disclosure to use any combination of the multiple anchor sutures of the invention during the same operation to allow ideal apposition of the entire avulsed soft tissue structure to bone.

The present invention is not to be limited in scope by the specific embodiments described herein. Modifications thereof will become apparent to those in the art based on the teachings of the foregoing description and drawings. Such modifications fall within the scope of the claimed invention.

What is claimed is:

1. A system for attaching soft tissue to bone including an assembly comprising:

(a) at least two anchors each having a region for insertion into the bone and a region for suture connection; and (b) a knotless suture attached to the suture connection region of each anchor.

2. A system as in claim 1 wherein at least one of the anchors is cannulated.

3. A system as in claim 1 wherein the suture is attached eccentrically to the insertion region of at least one of the anchors.

4. A system as in claim 1 having two anchors.

5. A system as in claim 4 having one suture.

6. A system as in claim 1 further comprising a gun for firing the assembly into soft tissue and bone.

7. A system as in claim 6 wherein the gun has at least one cannula.

8. A system as in claim 1 further comprising a grasper tool having at least one cannulated barrel.

9. A system as in claim 1 further comprising an initial anchor impactor tool having at least one cannula, a region adapted to receive an applied force, and a region adapted to apply force to at least one of the anchors.

10. A system as in claim 1 further comprising a final impactor tool having at least one cannula, a region adapted to receive an applied force, and a region adapted to apply force to at least one of the anchors.

11. The system of claim 1 wherein the region for suture connection on at least one anchor has a rotatable collar to prevent the suture from moving relative to the bone during rotation of the anchor, wherein the rotatable collar is positioned between the region for insertion into the bone and a region for receiving an applied force.

12. A method for attaching soft tissue to bone comprising:

(a) inserting at least two guide wires through the soft tissue and into the bone;

(b) inserting at least two anchors along the guide wires, the anchors being connected by at least one suture; and (c) inserting the anchors into the bone.

13. A method for attaching soft tissue to bone comprising:

providing an assembly for attaching soft tissue to bone, the assembly comprising at least two anchors, each anchor having an insertion region for insertion into the bone and a suture region for suture connection and a suture attached to the suture connection region of each anchor;

inserting the insertion region of each anchor into the bone while the suture is attached to the suture connection region of each anchor.

14. The system of claim 1 wherein the region for suture connection on at least one anchor has a rotatable collar to prevent the suture from moving relative to the bone during rotation of the anchor, wherein the anchor has a first portion and a second portion, the first portion having a region for receiving an applied force, and wherein the diameter of the rotatable collar is generally equal to the diameter of the first portion.

15. The system of claim 1 wherein the region for suture connection on at least one anchor has a rotatable collar to prevent the suture from moving relative to the bone during rotation of the anchor, wherein the rotatable collar is generally cylindrical.

* * * * *